US012775674B2

(12) United States Patent
Jones

(10) Patent No.: US 12,775,674 B2
(45) Date of Patent: Oct. 27, 2026

(54) DYNAMIC OUTLIER BIAS REDUCTION SYSTEM AND METHOD

(71) Applicant: THE HARTFORD STEAM BOILER INSPECTION AND INSURANCE COMPANY, Hartford, CT (US)

(72) Inventor: Richard B. Jones, Georgetown, TX (US)

(73) Assignee: THE HARTFORD STEAM BOILER INSPECTION AND INSURANCE COMPANY, Hartford, CT (US)

(*) Notice: Subject to any disclaimer, the term of this patent is extended or adjusted under 35 U.S.C. 154(b) by 257 days.

(21) Appl. No.: 18/407,017

(22) Filed: Jan. 8, 2024

(65) Prior Publication Data

US 2024/0152571 A1 May 9, 2024

Related U.S. Application Data

(63) Continuation of application No. 17/745,596, filed on May 16, 2022, now Pat. No. 11,868,425, which is a continuation of application No. 15/963,817, filed on Apr. 26, 2018, now Pat. No. 11,334,645, which is a continuation of application No. 14/738,266, filed on Jun. 12, 2015, now abandoned, which is a continuation of application No. 13/213,780, filed on Aug. 19, 2011, now Pat. No. 9,069,725.

(51) Int. Cl.

| | |
|---|---|
| ***G06F 17/10*** | (2006.01) |
| ***G01N 33/00*** | (2006.01) |
| ***G06F 17/18*** | (2006.01) |
| ***G06N 5/04*** | (2023.01) |
| *G06F 7/58* | (2006.01) |

(52) U.S. Cl.
CPC ......... *G06F 17/10* (2013.01); *G01N 33/0004* (2013.01); *G06F 17/18* (2013.01); *G06N 5/04* (2013.01); *G06F 7/588* (2013.01)

(58) Field of Classification Search
USPC .............................................................. 703/2
See application file for complete search history.

(56) References Cited

U.S. PATENT DOCUMENTS

2004/0172401 A1* 9/2004 Peace ...................... G06F 17/18
2011/0246409 A1* 10/2011 Mitra ...................... G06F 17/18
702/179

* cited by examiner

*Primary Examiner* — Bryce M Aisaka
(74) *Attorney, Agent, or Firm* — Grogan, Tuccillo & Vanderleeden, LLP

(57) ABSTRACT

A system and method is described herein for data filtering to reduce functional, and trend line outlier bias. Outliers are removed from the data set through an objective statistical method. Bias is determined based on absolute, relative error, or both. Error values are computed from the data, model coefficients, or trend line calculations. Outlier data records are removed when the error values are greater than or equal to the user-supplied criteria. For optimization methods or other iterative calculations, the removed data are re-applied each iteration to the model computing new results. Using model values for the complete dataset, new error values are computed and the outlier bias reduction procedure is re-applied. Overall error is minimized for model coefficients and outlier removed data in an iterative fashion until user defined error improvement limits are reached. The filtered data may be used for validation, outlier bias reduction and data quality operations.

12 Claims, 8 Drawing Sheets

Data Outlier Bias Reduction Method

FIG 2

| Step 210 | Step 220 | | Step 230 | | Step 240 | | | Step 250 | | Step 260 | |
|---|---|---|---|---|---|---|---|---|---|---|---|
| Initial Data | Ranked Data | Ranked Function Calculation | Error Calculations | | Percentile-Based Quality Criteria | | | Quality Screened Data | | Outlier Bias Reduced Function Value | Full Data Function Value |
| | | Function: (Arithmetic Average) | Relative Error | Absolute Error | | Quality Criteria % | Quality Criteria Value | Admitted / Removed (1/0) | Validated Data | 0.546 | 0.569 |
| 0.576 | 0.030 | 0.030 | 0.94336 | 0.000 | Relative Error | 90% | 0.215 | 0 | | | |
| 0.339 | 0.088 | 0.059 | 0.28177 | 0.001 | Absolute Error | 90% | 0.003 | 0 | | | |
| 0.433 | 0.153 | 0.091 | 0.20717 | 0.001 | | | | 1 | 0.153 | | |
| 0.403 | 0.255 | 0.132 | 0.05772 | 0.002 | | | | 1 | 0.255 | | |
| 0.567 | 0.290 | 0.163 | 0.03192 | 0.001 | | | | 1 | 0.290 | | |
| 0.701 | 0.339 | 0.193 | 0.02442 | 0.001 | | | | 1 | 0.339 | | |
| 0.514 | 0.403 | 0.223 | 0.01393 | 0.001 | | | | 1 | 0.403 | | |
| 0.290 | 0.433 | 0.249 | 0.00738 | 0.001 | | | | 1 | 0.433 | | |
| 0.255 | 0.441 | 0.270 | 0.00815 | 0.000 | | | | 1 | 0.441 | | |
| 0.765 | 0.514 | 0.295 | 0.00708 | 0.001 | | | | 1 | 0.514 | | |
| 0.618 | 0.567 | 0.320 | 0.00446 | 0.001 | | | | 1 | 0.567 | | |
| 0.775 | 0.576 | 0.341 | 0.00392 | 0.000 | | | | 1 | 0.576 | | |
| 0.909 | 0.618 | 0.362 | 0.00364 | 0.000 | | | | 1 | 0.618 | | |
| 0.088 | 0.668 | 0.384 | 0.00271 | 0.000 | | | | 1 | 0.668 | | |
| 0.153 | 0.684 | 0.404 | 0.00211 | 0.000 | | | | 1 | 0.684 | | |
| 2.000 | 0.701 | 0.423 | 0.00200 | 0.000 | | | | 1 | 0.701 | | |
| 0.744 | 0.744 | 0.442 | 0.00166 | 0.000 | | | | 1 | 0.744 | | |
| 0.684 | 0.765 | 0.460 | 0.00130 | 0.000 | | | | 1 | 0.765 | | |
| 0.668 | 0.775 | 0.476 | 0.00206 | 0.000 | | | | 1 | 0.775 | | |
| 0.441 | 0.909 | 0.498 | 0.02066 | 0.000 | | | | 1 | 0.909 | | |
| 0.030 | 2.000 | 0.569 | | 0.005 | | | | 0 | | | |

FIG 3

| Step 310 | | Step 320 | | Step 330 | | | Step 340 | | | Step 350 | |
|---|---|---|---|---|---|---|---|---|---|---|---|
| Initial Data Values | | Error Calculations | | Data Validation Criteria | | | Validated Dataset | | | Results Comparison | |
| Data Set 1 | Data Set 2 | Relative Error | Absolute Error | | Quality Criteria % | Quality Criteria Value | Admitted / Removed (1/0) | Quality Screened Data Values | | Outlier Bias Reduction Pearson Coefficient | Original Pearson Coefficient |
| 68,991 | 26,105 | 0.386 | 1.8E+09 | Relative Error | 90% | 0.945 | 1 | 68,991 | 26,105 | 0.933 | 0.916 |
| 8,446 | 8,997 | 0.004 | 3.0E+05 | Absolute Error | 90% | 8,439,995 | 1 | 8,446 | 8,997 | | |
| 2,833 | 3,980 | 0.164 | 1.3E+06 | | | | 1 | 2,833 | 3,980 | | |
| 3,581 | 7,722 | 1.338 | 1.7E+07 | | | | 0 | | | | |
| 3,021 | 1,040 | 0.430 | 3.9E+06 | | | | 1 | 3,021 | 1,040 | | |
| 8,683 | 6,904 | 0.042 | 3.2E+06 | | | | 1 | 8,693 | 6,904 | | |
| 2,788 | 4,654 | 0.448 | 3.5E+06 | | | | 1 | 2,788 | 4,654 | | |
| 1,625 | 878 | 0.211 | 5.6E+05 | | | | 1 | 1,625 | 878 | | |
| 1,133 | 822 | 0.075 | 9.6E+04 | | | | 1 | 1,133 | 822 | | |
| 1,635 | 2,715 | 0.436 | 1.2E+06 | | | | 1 | 1,635 | 2,715 | | |
| 2,375 | 4,630 | 0.902 | 5.1E+06 | | | | 1 | 2,375 | 4,630 | | |
| 1,044 | 1,493 | 0.185 | 2.0E+05 | | | | 1 | 1,044 | 1,493 | | |
| 1,308 | 619 | 0.278 | 4.8E+05 | | | | 1 | 1,308 | 619 | | |
| 1,561 | 3,695 | 1.870 | 4.6E+06 | | | | 0 | | | | |
| 1,265 | 1,292 | 0.000 | 6.8E+02 | | | | 1 | 1,265 | 1,292 | | |
| 1,047 | 1,686 | 0.371 | 4.1E+05 | | | | 1 | 1,047 | 1,686 | | |
| 723 | 1,360 | 0.777 | 4.1E+05 | | | | 1 | 723 | 1,360 | | |
| 3,213 | 1,219 | 0.385 | 4.0E+06 | | | | 1 | 3,213 | 1,219 | | |
| 1,475 | 2,047 | 0.151 | 3.3E+05 | | | | 1 | 1,475 | 2,047 | | |
| 1,460 | 2,813 | 0.858 | 1.8E+06 | | | | 1 | 1,460 | 2,813 | | |
| 980 | 377 | 0.379 | 3.6E+05 | | | | 1 | 980 | 377 | | |
| 1,157 | 500 | 0.322 | 4.3E+05 | | | | 1 | 1,157 | 500 | | |
| 1,166 | 757 | 0.123 | 1.7E+05 | | | | 1 | 1,166 | 757 | | |
| 1,628 | 89 | 0.894 | 2.4E+06 | | | | 1 | 1,628 | 89 | | |
| 1,466 | 1,291 | 0.014 | 3.1E+04 | | | | 1 | 1,466 | 1,291 | | |
| 5,586 | 8,450 | 0.263 | 8.2E+06 | | | | 1 | 5,586 | 8,450 | | |
| 4,181 | 4,030 | 0.001 | 2.3E+04 | | | | 1 | 4,181 | 4,030 | | |
| 1,659 | 2,290 | 0.145 | 4.0E+05 | | | | 1 | 1,659 | 2,290 | | |
| 3,072 | 3,576 | 0.027 | 2.5E+05 | | | | 1 | 3,072 | 3,576 | | |
| 860 | 479 | 0.197 | 1.5E+05 | | | | 1 | 860 | 479 | | |
| 1,752 | 280 | 0.706 | 2.2E+06 | | | | 1 | 1,752 | 280 | | |
| 1,786 | 2,146 | 0.041 | 1.3E+05 | | | | 1 | 1,786 | 2,146 | | |
| 1,511 | 577 | 0.383 | 8.7E+05 | | | | 1 | 1,511 | 577 | | |
| 2,467 | 2,815 | 0.020 | 1.2E+05 | | | | 1 | 2,467 | 2,815 | | |

Random Dataset: Outlier Bias Reduction (70%)
~30% of Data Removed as Outliers

Realistic Model Dataset: Outlier Bias Reduction (70%)
~30% of Data Removed as Outliers Random Dataset: Outlier Bias Reduction (50%)
~50% of Data Removed as Outliers Realistic Model Dataset: Outlier Bias Reduction (50%)
~50% of Data Removed as Outliers

DYNAMIC OUTLIER BIAS REDUCTION SYSTEM AND METHOD

FIELD OF THE INVENTION

The present invention relates to the analysis of data where outlier elements are removed (or filtered) from the analysis development. The analysis may be related to the computation of simple statistics or more complex operations involving mathematical models that use data in their development. The purpose of outlier data filtering may be to perform data quality and data validation operations, or to compute representative standards, statistics, data groups that have applications in subsequent analyses, regression analysis, time series analysis or qualified data for mathematical models development.

BACKGROUND

Removing outlier data in standards or data-driven model development is an important part of the pre-analysis work to ensure a representative and fair analysis is developed from the underlying data. For example, developing equitable benchmarking of greenhouse gas standards for carbon dioxide ($CO_2$), ozone ($O_3$), water vapor ($H_2O$), hydrofluorocarbons (HFCs), perfluorocarbons (PFCs), chlorofluorocarbons (CFCs), sulfur hexafluoride ($SF_6$), methane ($CH_4$), nitrous oxide ($N_2O$), carbon monoxide (CO), nitrogen oxides (NOx), and non-methane volatile organic compounds (NMVOCs) emissions requires that collected industrial data used in the standards development exhibit certain properties. Extremely good or bad performance by a few of the industrial sites should not bias the standards computed for other sites. It may be judged unfair or unrepresentative to include such performance results in the standard calculations. In the past, the performance outliers were removed via a semi-quantitative process requiring subjective input. The present system and method is a data-driven approach that performs this task as an integral part of the model development, and not at the pre-analysis or pre-model development stage.

The removal of bias can be a subjective process wherein justification is documented in some form to substantiate data changes. However, any form of outlier removal is a form of data censoring that carries the potential for changing calculation results. Such data filtering may or may not reduce bias or error in the calculation and in the spirit of full analysis disclosure, strict data removal guidelines and documentation to remove outliers needs to be included with the analysis results. Therefore, there is a need in the art to provide a new system and method for objectively removing outlier data bias using a dynamic statistical process useful for the purposes of data quality operations, data validation, statistic calculations or mathematical model development, etc. The outlier bias removal system and method can also be used to group data into representative categories where the data is applied to the development of mathematical models customized to each group. In a preferred embodiment, coefficients are defined as multiplicative and additive factors in mathematical models and also other numerical parameters that are nonlinear in nature. For example, in the mathematical model, $f(x,y,z)=a*x+b*y^c+d*\sin(ez)+f$, a, b, c, d, e, and f are all defined as coefficients. The values of these terms may be fixed or part of the development of the mathematical model.

BRIEF SUMMARY

A preferred embodiment includes a computer implemented method for reducing outlier bias comprising the steps of: selecting a bias criteria; providing a data set; providing a set of model coefficients; selecting a set of target values; (1) generating a set of predicted values for the complete data set; (2) generating an error set for the dataset; (3) generating a set of error threshold values based on the error set and the bias criteria; (4) generating, by a processor, a censored data set based on the error set and the set of error threshold values; (5) generating, by the processor, a set of new model coefficients; and (6) using the set of new model coefficients, repeating steps (1)-(5), unless a censoring performance termination criteria is satisfied. In a preferred embodiment, the set of predicted values may be generated based on the data set and the set of model coefficients. In a preferred embodiment, the error set may comprise a set of absolute errors and a set of relative errors, generated based on the set of predicted values and the set of target values. In another embodiment, the error set may comprise values calculated as the difference between the set of predicted values and the set of target values. In another embodiment, the step of generating the set of new coefficients may further comprise the step of minimizing the set of errors between the set of predicted values and the set of actual values, which can be accomplished using a linear, or a non-linear optimization model. In a preferred embodiment, the censoring performance termination criteria may be based on a standard error and a coefficient of determination.

Another embodiment includes a computer implemented method for reducing outlier bias comprising the steps of: selecting an error criteria; selecting a data set; selecting a set of actual values; selecting an initial set of model coefficients; generating a set of model predicted values based on the complete data set and the initial set of model coefficients; (1) generating a set of errors based on the model predicted values and the set of actual values for the complete dataset; (2) generating a set of error threshold values based on the complete set of errors and the error criteria for the complete data set; (3) generating an outlier removed data set, wherein the filtering is based on the complete data set and the set of error threshold values; (4) generating a set of new coefficients based on the filtered data set and the set of previous coefficients, wherein the generation of the set of new coefficients is performed by the computer processor; (5) generating a set of outlier bias reduced model predicted values based on the filtered data set and the set of new model coefficients, wherein the generation of the set of outlier bias reduced model predicted values is performed by a computer processor; (6) generating a set of model performance values based on the model predicted values and the set of actual values; repeating steps (1)-(6), while substituting the set of new coefficients for the set of coefficients from the previous iteration, unless: a performance termination criteria is satisfied; and storing the set of model predicted values in a computer data medium.

Another embodiment includes a computer implemented method for reducing outlier bias comprising the steps of: selecting a target variable for a facility; selecting a set of actual values of the target variable; identifying a plurality of variables for the facility that are related to the target variable; obtaining a data set for the facility, the data set comprising values for the plurality of variables; selecting a bias criteria; selecting a set of model coefficients; (1) generating a set of predicted values based on the complete data set and the set of model coefficients; (2) generating a set of censoring model performance values based on the set of predicted values and the set of actual values; (3) generating an error set based on the set of predicted values and the set of actual values for the target variable; (4) generating a set of error threshold values based on the error set and the bias criteria; (5) generating, by a processor, a censored data set based on the data set and the set of error thresholds; (6) generating, by the processor, a set of new model coefficients based on the censored data set and the set of model coefficients; (7) generating, by the processor, a set of new predicted values based on the data set and the set of new model coefficients; (8) generating a set of new censoring model performance values based on the set of new predicted values and the set of actual values; using the set of new coefficients, repeating steps (1)-(8) unless a censoring performance termination criteria is satisfied; and storing the set of new model predicted values in a computer data medium.

Another embodiment includes a computer implemented method for reducing outlier bias comprising the steps of: determining a target variable for a facility, wherein the target variable is a metric for an industrial facility related to its production, financial performance, or emissions; identifying a plurality of variables for the facility, wherein the plurality of variables comprises: a plurality of direct variables for the facility that influence the target variable; and a set of transformed variables for the facility, each transformed variable is a function of at least one direct facility variable that influences the target variable; selecting an error criteria comprising: an absolute error, and a relative error; obtaining a data set for the facility, wherein the data set comprises values for the plurality of variables; selecting a set of actual values of the target variable; selecting an initial set of model coefficients; generating a set of model predicted values based on the complete data set and the initial set of model coefficients; generating a complete set of errors based on the set of model predicted values and the set of actual values, wherein the relative error is calculated using the formula: Relative $\text{Error}_m=((\text{Predicted Value}_m-\text{Actual Value}_m)/\text{Actual Value}_m)^2$ wherein 'm' is a reference number, and wherein the absolute error is calculated using the formula: Absolute $\text{Error}_m=(\text{Predicted Value}_m-\text{Actual Value}_m)^2$; generating a set of model performance values based on the set of model predicted values and the set of actual values, wherein the set of overall model performance values comprises of: a first standard error, and a first coefficient of determination; (1) generating a set of errors based on the model predicted values and the set of actual values for the complete dataset; (2) generating a set of error threshold values based on the complete set of errors and the error criteria for the complete data set; (3) generating an outlier removed data set by removing data with error values greater than or equal to the error threshold values, wherein the filtering is based on the complete data set and the set of error threshold values; (4) generating a set of outlier bias reduced model predicted values based on the outlier removed data set and the set of model coefficients by minimizing the error between the set of predicted values and the set of actual values using at least one of: a linear optimization model, and a nonlinear optimization model, wherein the generation of the new model predicted values is performed by a computer processor; (5) generating a set of new coefficients based on the outlier removed data set and the previous set of coefficients, wherein the generation of the set of new coefficients is performed by the computer processor; (6) generating a set of overall model performance values based on the set of new predicted model values and the set of actual values, wherein the set of model performance values comprise: a second standard error, and a second coefficient of determination; repeating steps (1)-(6), while substituting the set of new coefficients for the set of coefficients from the previous iteration, unless: a performance termination criteria is satisfied, wherein the performance termination criteria comprises: a standard error termination value and a coefficient of determination termination value, and wherein satisfying the performance termination criteria comprises: the standard error termination value is greater than the difference between the first and second standard error, and the coefficient of determination termination value is greater than the difference between the first and second coefficient of determination; and storing the set of new model predicted values in a computer data medium.

Another embodiment includes a computer implemented method for reducing outlier bias comprising the steps of: selecting an error criteria; selecting a data set; selecting a set of actual values; selecting an initial set of model predicted values; determining a set of errors based on the set of model predicted values and the set of actual values; (1) determining a set of error threshold values based on the complete set of errors and the error criteria; (2) generating an outlier removed data set, wherein the filtering is based on the data set and the set of error threshold values; (3) generating a set of outlier bias reduced model predicted values based on the outlier removed data set and the previous model predicted values, wherein the generation of the set of outlier bias reduced model predicted values is performed by a computer processor; (4) determining a set of errors based on the set of new model predicted values and the set of actual values; repeating steps (1)-(4), while substituting the set of new model predicted values for the set of model predicted values from the previous iteration, unless: a performance termination criteria is satisfied; and storing the set of outlier bias reduced model predicted values in a computer data medium.

Another embodiment includes a computer implemented method for reducing outlier bias comprising the steps of: determining a target variable for a facility; identifying a plurality of variables for the facility, wherein the plurality of variables comprises: a plurality of direct variables for the facility that influence the target variable; and a set of transformed variables for the facility, each transformed variable being a function of at least one direct facility variable that influences the target variable; selecting an error criteria comprising: an absolute error, and a relative error; obtaining a data set, wherein the data set comprises values for the plurality of variables, and selecting a set of actual values of the target variable; selecting an initial set of model coefficients; generating a set of model predicted values by applying a set of model coefficients to the data set Absolute $\text{Error}_k=(\text{Model Results}_k-\text{Actual Emissions}_k)^2$; determining a set of performance values based on the set of model predicted values and the set of actual values, wherein the set of performance values comprises: a first standard error, and a first coefficient of determination; (1) generating a set of errors based on the set of model predicted values and the set of actual values for the complete dataset, wherein the relative error is calculated using the formula: Relative $\text{Error}_m=((\text{Predicted Value}_m-\text{Actual Value}_m)/\text{Actual Value}_m)^2$, wherein 'm' is a reference number, and wherein the absolute error is calculated using the formula: Absolute $\text{Error}_m=(\text{Predicted Value}_m-\text{Actual Value}_m)^2$) (2) generating a set of error threshold values based on the complete set of errors and the error criteria for the complete data set; (3) generating an outlier removed data set by removing data with error values greater than or equal to the set of error threshold values, wherein the filtering is based on the data set and the set of error threshold values; (4) generating a set of new coefficients based on the outlier removed data set and the set of previous coefficients (5) generating a set of outlier bias reduced model predicted values based on the outlier removed data set and the set of new model coefficient by minimizing the error between the set of predicted values and the set of actual values using at least one of: a linear optimization model, and a nonlinear optimization model, wherein the generation of the model predicted values is performed by a computer processor; (6) generating a set of updated performance values based on the set of outlier bias reduced model predicted values and the set of actual values, wherein the set of updated performance values comprises: a second standard error, and a second coefficient of determination; repeating steps (1)-(6), while substituting the set of new coefficients for the set of coefficients from the previous iteration, unless: a performance termination criteria is satisfied, wherein the performance termination criteria comprises: a standard error termination value, and a coefficient of determination termination value, and wherein satisfying the performance termination criteria comprises the standard error termination value is greater than the difference between the first and second standard error, and the coefficient of determination termination value is greater than the difference between the first and second coefficient of determination; and storing the set of outlier bias reduction factors in a computer data medium.

Another embodiment includes a computer implemented method for assessing the viability of a data set as used in developing a model comprising the steps of: providing a target data set comprising a plurality of data values; generating a random target data set based on the target dataset; selecting a set of bias criteria values; generating, by a processor, an outlier bias reduced target data set based on the data set and each of the selected bias criteria values; generating, by the processor, an outlier bias reduced random data set based on the random data set and each of the selected bias criteria values; calculating a set of error values for the outlier bias reduced data set and the outlier bias reduced random data set; calculating a set of correlation coefficients for the outlier bias reduced data set and the outlier bias reduced random data set; generating bias criteria curves for the data set and the random data set based on the selected bias criteria values and the corresponding error value and correlation coefficient; and comparing the bias criteria curve for the data set to the bias criteria curve for the random data set. The outlier bias reduced target data set and the outlier bias reduced random target data set are generated using the Dynamic Outlier Bias Removal methodology. The random target data set can comprise of randomized data values developed from values within the range of the plurality of data values. Also, the set of error values can comprise a set of standard errors, and wherein the set of correlation coefficients comprises a set of coefficient of determination values. Another embodiment can further comprise the step of generating automated advice regarding the viability of the target data set to support the developed model, and vice versa, based on comparing the bias criteria curve for the target data set to the bias criteria curve for the random target data set. Advice can be generated based on parameters selected by analysts, such as a correlation coefficient threshold and/or an error threshold. Yet another embodiment further comprises the steps of: providing an actual data set comprising a plurality of actual data values corresponding to the model predicted values; generating a random actual data set based on the actual data set; generating, by a processor, an outlier bias reduced actual data set based on the actual data set and each of the selected bias criteria values; generating, by the processor, an outlier bias reduced random actual data set based on the random actual data set and each of the selected bias criteria values; generating, for each selected bias criteria, a random data plot based on the outlier bias reduced random target data set and the outlier bias reduced random actual data; generating, for each selected bias criteria, a realistic data plot based on the outlier bias reduced target data set and the outlier bias reduced actual target data set; and comparing the random data plot with the realistic data plot corresponding to each of the selected bias criteria.

A preferred embodiment includes a system comprising: a server, comprising: a processor, and a storage subsystem; a database stored by the storage subsystem comprising: a data set; and a computer program stored by the storage subsystem comprising instructions that, when executed, cause the processor to: select a bias criteria; provide a set of model coefficients; select a set of target values; (1) generate a set of predicted values for the data set; (2) generate an error set for the dataset; (3) generate a set of error threshold values based on the error set and the bias criteria; (4) generate a censored data set based on the error set and the set of error threshold values; (5) generate a set of new model coefficients; and (6) using the set of new model coefficients, repeat steps (1)-(5), unless a censoring performance termination criteria is satisfied. In a preferred embodiment, the set of predicted values may be generated based on the data set and the set of model coefficients. In a preferred embodiment, the error set may comprise a set of absolute errors and a set of relative errors, generated based on the set of predicted values and the set of target values. In another embodiment, the error set may comprise values calculated as the difference between the set of predicted values and the set of target values. In another embodiment, the step of generating the set of new coefficients may further comprise the step of minimizing the set of errors between the set of predicted values and the set of actual values, which can be accomplished using a linear, or a non-linear optimization model. In a preferred embodiment, the censoring performance termination criteria may be based on a standard error and a coefficient of determination.

Another embodiment of the present invention includes a system comprising: a server, comprising: a processor, and a storage subsystem; a database stored by the storage subsystem comprising: a data set; and a computer program stored by the storage subsystem comprising instructions that, when executed, cause the processor to: select an error criteria; select a set of actual values; select an initial set of coefficients; generate a complete set of model predicted values from the data set and the initial set of coefficients; (1) generate a set of errors based on the model predicted values and the set of actual values for the complete dataset; (2) generate a set of error threshold values based on the complete set of errors and the error criteria for the complete data set; (3) generate an outlier removed data set, wherein the filtering is based on the complete data set and the set of error threshold values; (4) generate a set of outlier bias reduced model predicted values based on the outlier removed data set and the set of coefficients, wherein the generation of the set of outlier bias reduced model predicted values is performed by a computer processor; (5) generate a set of new coefficients based on the outlier removed data set and the set of previous coefficients, wherein the generation of the set of new coefficients is performed by the computer processor; (6) generate a set of model performance values based on the outlier bias reduced model predicted values and the set of actual values; repeat steps (1)-(6), while substituting the set of new coefficients for the set of coefficients from the previous iteration, unless: a performance termination criteria is satisfied; and store the set of overall outlier bias reduction model predicted values in a computer data medium.

Yet another embodiment includes a system comprising: a server, comprising: a processor, and a storage subsystem; a database stored by the storage subsystem comprising: a target variable for a facility; a set of actual values of the target variable; a plurality of variables for the facility that are related to the target variable; a data set for the facility, the data set comprising values for the plurality of variables; and a computer program stored by the storage subsystem comprising instructions that, when executed, cause the processor to: select a bias criteria; select a set of model coefficients; (1) generate a set of predicted values based on the data set and the set of model coefficients; (2) generate a set of censoring model performance values based on the set of predicted values and the set of actual values; (3) generate an error set based on the set of predicted values and the set of actual values for the target variable; (4) generate a set of error threshold values based on the error set and the bias criteria; (5) generate a censored data set based on the data set and the set of error thresholds; (6) generate a set of new model coefficients based on the censored data set and the set of model coefficients; (7) generate a set of new predicted values based on the data set and the set of new model coefficients; (8) generate a set of new censoring model performance values based on the set of new predicted values and the set of actual values; using the set of new coefficients, repeat steps (1)-(8) unless a censoring performance termination criteria is satisfied; and storing the set of new model predicted values in the storage subsystem.

Another embodiment includes a system comprising: a server, comprising: a processor, and a storage subsystem; a database stored by the storage subsystem comprising: a data set for a facility; and a computer program stored by the storage subsystem comprising instructions that, when executed, cause the processor to: determine a target variable; identify a plurality of variables, wherein the plurality of variables comprises: a plurality of direct variables for the facility that influence the target variable; and a set of transformed variables for the facility, each transformed variables being a function of at least one direct variable that influences the target variable; select an error criteria comprising: an absolute error, and a relative error; select a set of actual values of the target variable; select an initial set of coefficients; generate a set of model predicted values based on the data set and the initial set of coefficients; determine a set of errors based on the set of model predicted values and the set of actual values, wherein the relative error is calculated using the formula: Relative $\text{Error}_m$=((Predicted $\text{Value}_m$−Actual $\text{Value}_m$)/Actual $\text{Value}_m)^2$, wherein 'm' is a reference number, and wherein the absolute error is calculated using the formula: Absolute $\text{Error}_m$=(Predicted $\text{Value}_m$−Actual $\text{Value}_m)^2$ Absolute $\text{Error}_k$=(Model $\text{Results}_k$−Actual $\text{Emissions}_k)^2$; determine a set of performance values based on the set of model predicted values and the set of actual values; wherein the set of performance values comprises: a first standard error, and a first coefficient of determination; (1) generate a set of errors based on the model predicted values and the set of actual values; (2) generating a set of error threshold values based on the complete set of errors and the error criteria for the complete data set; (3) generate an outlier removed data set by filtering data with error values outside the set of error threshold values, wherein the filtering is based on the data set and the set of error threshold values; (4) generate a set of new model predicted values based on the outlier removed data set and the set of coefficients by minimizing an error between the set of model predicted values and the set of actual values using at least one of: a linear optimization model, and a nonlinear optimization model, wherein the generation of the outlier bias reduced model predicted values is performed by a computer processor; (5) generate a set of new coefficients based on the outlier removed data set and the set of previous coefficients, wherein the generation of the set of new coefficients is performed by the computer processor; (6) generate a set of performance values based on the set of new model predicted values and the set of actual values; wherein the set of model performance values comprises: a second standard error, and a second coefficient of determination; repeat steps (1)-(6), while substituting the set of new coefficients for the set of coefficients from the previous iteration, unless: a performance termination criteria is satisfied, wherein the performance termination criteria comprises: a standard error, and a coefficient of determination, and wherein satisfying the performance termination criteria comprises: the standard error termination value is greater than the difference between the first and second standard error, and the coefficient of determination termination value is greater than the difference between the first and second coefficient of determination; and store the set of new model predicted values in a computer data medium.

Another embodiment of the present invention includes a system comprising: a server, comprising: a processor, and a storage subsystem; a database stored by the storage subsystem comprising: a data set, a computer program stored by the storage subsystem comprising instructions that, when executed, cause the processor to: select an error criteria; select a data set; select a set of actual values; select an initial set of model predicted values; determine a set of errors based on the set of model predicted values and the set of actual values; (1) determine a set of error threshold values based on the complete set of errors and the error criteria; (2) generate an outlier removed data set, wherein the filtering is based on the data set and the set of error threshold values; (3) generate a set of outlier bias reduced model predicted values based on the outlier removed data set and the complete set of model predicted values, wherein the generation of the set of outlier bias reduced model predicted values is performed by a computer processor; (4) determine a set of errors based on the set of outlier bias reduction model predicted values and the corresponding set of actual values; repeat steps (1)-(4), while substituting the set of outlier bias reduction model predicted values for the set of model predicted values unless: a performance termination criteria is satisfied; and store the set of outlier bias reduction factors in a computer data medium.

Another embodiment of the present invention includes a system comprising: a server, comprising: a processor, and a storage subsystem; a database stored by the storage subsystem comprising: a data set, a computer program stored by the storage subsystem comprising instructions that, when executed, cause the processor to: determine a target variable; identify a plurality of variables for the facility, wherein the plurality of variables comprises: a plurality of direct variables for the facility that influence the target variable; and a set of transformed variables for the facility, each transformed variable is a function of at least one primary facility variable that influences the target variable; select an error criteria comprising: an absolute error, and a relative error; obtain a data set, wherein the data set comprises values for the plurality of variables, and select a set of actual values of the target variable; select an initial set of coefficients; generate a set of model predicted values by applying the set of model coefficients to the data set; determine a set of performance values based on the set of model predicted values and the set of actual values, wherein the set of performance values comprises: a first standard error, and a first coefficient of determination; (1) determine a set of errors based on the set of model predicted values and the set of actual values, wherein the relative error is calculated using the formula: Relative $\text{Error}_k$=((Predicted $\text{Value}_k$−Actual $\text{Value}_k$)/Actual $\text{Value}_k$)$^2$, wherein 'k' is a reference number, and wherein the absolute error is calculated using the formula: Absolute $\text{Error}_k$=(Predicted $\text{Value}_k$−Actual $\text{Value}_k$)$^2$ Absolute $\text{Error}_k$=(Model $\text{Results}_k$−Actual $\text{Emissions}_k$)$^2$; (2) determine a set of error threshold values based on the set of errors and the error criteria for the complete data set; (3) generate an outlier removed data set by removing data with error values greater than or equal to the error threshold values, wherein the filtering is based on the data set and the set of error threshold values; (4) generate a set of new coefficients based on the outlier removed dataset and the set of previous coefficients; (5) generate a set of outlier bias reduced model values based on the outlier removed data set and the set of coefficients and minimizing an error between the set of predicted values and the set of actual values using at least one of: a linear optimization model, and a nonlinear optimization model; (5) determine a set of updated performance values based on the set of outlier bias reduced model predicted values and the set of actual values, wherein the set of updated performance values comprises: a second standard error, and a second coefficient of determination; repeat steps (1)-(5), while substituting the set of new coefficients for the set of coefficients from the previous iteration, unless: a performance termination criteria is satisfied, wherein the performance termination criteria comprises: a standard error termination value, and a coefficient of determination termination value, and wherein satisfying the performance termination criteria comprises the standard error termination value is greater than the difference between the first and second standard error, and the coefficient of determination termination value is greater than the difference between the first and second coefficient of determination; and storing the set of outlier bias reduction factors in a computer data medium.

Yet another embodiment includes a system for assessing the viability of a data set as used in developing a model comprising: a server, comprising: a processor, and a storage subsystem; a database stored by the storage subsystem comprising: a target data set comprising a plurality of model predicted values; a computer program stored by the storage subsystem comprising instructions that, when executed, cause the processor to: generate a random target data set; select a set of bias criteria values; generate outlier bias reduced data sets based on the target data set and each of the selected bias criteria values; generate an outlier bias reduced random target data set based on the random target data set and each of the selected bias criteria values; calculate a set of error values for the outlier bias reduced target data set and the outlier bias reduced random target data set; calculate a set of correlation coefficients for the outlier bias reduced target data set and the outlier bias reduced random target data set; generate bias criteria curves for the target data set and the random target data set based on the corresponding error value and correlation coefficient for each selected bias criteria; and compare the bias criteria curve for the target data set to the bias criteria curve for the random target data set. The processor generates the outlier bias reduced target data set and the outlier bias reduced random target data set using the Dynamic Outlier Bias Removal methodology. The random target data set can comprise of randomized data values developed from values within the range of the plurality of data values. Also, the set of error values can comprise a set of standard errors, and the set of correlation coefficients comprises a set of coefficient of determination values. In another embodiment, the program further comprises instructions that, when executed, cause the processor to generate automated advice based on comparing the bias criteria curve for the target data set to the bias criteria curve for the random target data set. Advice can be generated based on parameters selected by analysts, such as a correlation coefficient threshold and/or an error threshold. In yet another embodiment, the system's database further comprises an actual data set comprising a plurality of actual data values corresponding to the model predicted values, and the program further comprises instructions that, when executed, cause the processor to: generate a random actual data set based on the actual data set; generate an outlier bias reduced actual data set based on the actual data set and each of the selected bias criteria values; generate an outlier bias reduced random actual data set based on the random actual data set and each of the selected bias criteria values; generate, for each selected bias criteria, a random data plot based on the outlier bias reduced random target data set and the outlier bias reduced random actual data; generate, for each selected bias criteria, a realistic data plot based on the outlier bias reduced target data set and the outlier bias reduced actual target data set; and compare the random data plot with the realistic data plot corresponding to each of the selected bias criteria.

BRIEF DESCRIPTION OF THE DRAWINGS

FIG. 2 is a flowchart illustrating an embodiment of the data outlier identification and removal method for data quality operations.

FIG. 3 is a flowchart illustrating an embodiment of the data outlier identification and removal method for data validation.

DETAILED DESCRIPTION OF THE INVENTION

Figure 1:
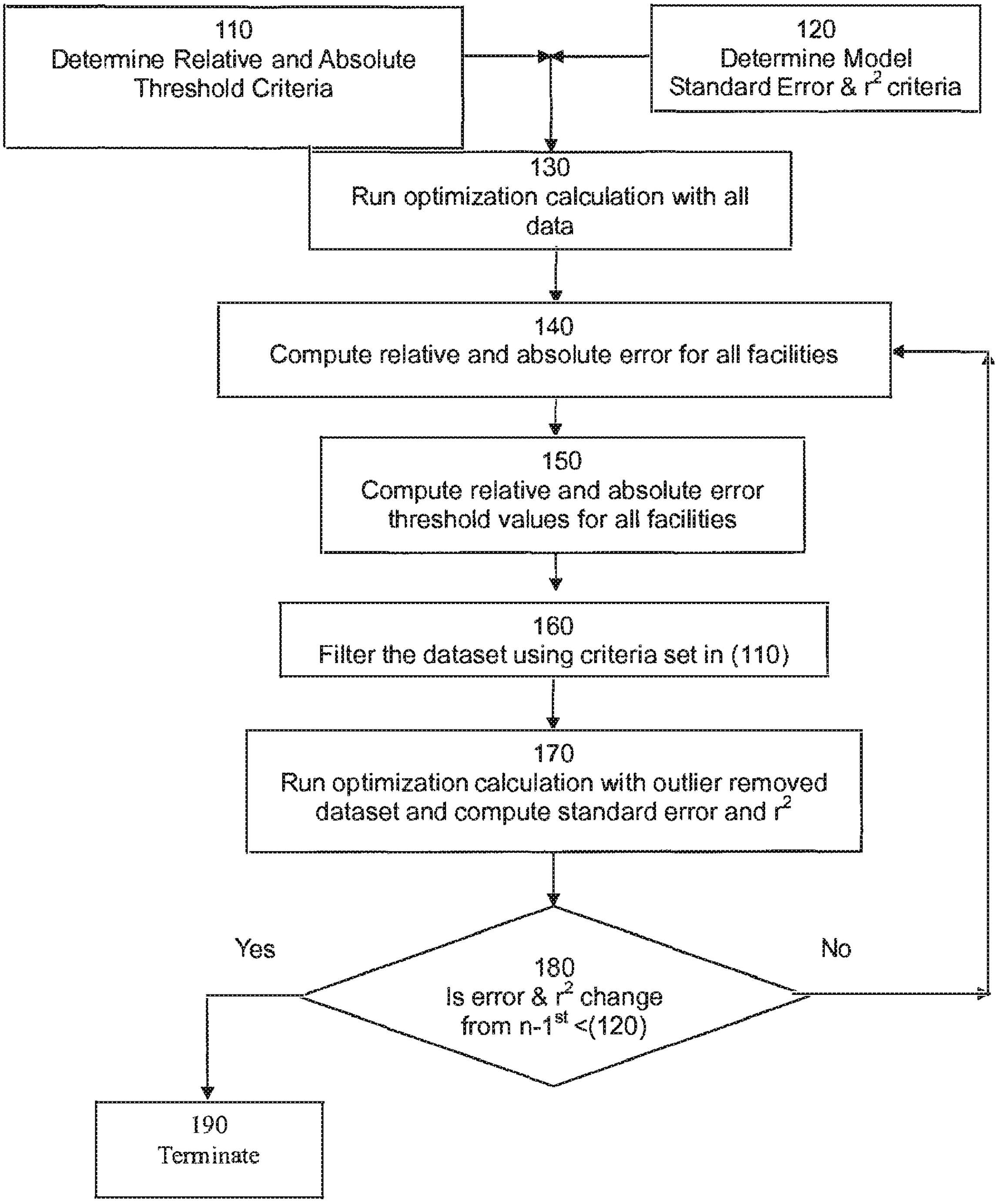
FIG. 1 is a flowchart illustrating an embodiment of the data outlier identification and removal method.

The following disclosure provides many different embodiments, or examples, for implementing different features of a system and method for accessing and managing structured content. Specific examples of components, processes, and implementations are described to help clarify the invention. These are merely examples and are not intended to limit the invention from that described in the claims.

Well-known elements are presented without detailed description so as not to obscure the preferred embodiments of the present invention with unnecessary detail. For the most part, details unnecessary to obtain a complete understanding of the preferred embodiments of the present invention have been omitted inasmuch as such details are within the skills of persons of ordinary skill in the relevant art.

A mathematical description of one embodiment of Dynamic Outlier Bias Reduction is shown as follows:

Nomenclature $\hat{X}$—Set of all data records: $\hat{X}=\hat{X}_k+\hat{X}_{Ck}$, where:
- $\hat{X}_k$—Set of accepted data records for the $k^{th}$ iteration
- $\hat{X}_{Ck}$—Set of outlier (removed) data records for the $k^{th}$ iteration $\hat{Q}_k$—Set of computed model predicted values for $\hat{Q}_k$ $\hat{Q}_{Ck}$—Set of outlier model predicted values for data records, $\hat{Q}_{Ck}$ $\hat{A}$—Set of actual values (target values) on which the model is based $\hat{\beta}_{k\to k+1}$—Set of model coefficients at the $k+1^{st}$ iteration computed as a result of the model computations using $\hat{X}_k$ $M(\hat{X}_k:\hat{\beta}_{k\to k+1})$—Model computation producing $\hat{Q}_{k+1}$ from $\hat{X}_k$ storing model derived and user-supplied coefficients: $\hat{\beta}_{k\to k+1}$ C—User supplied error criteria (%)

$\Psi(\hat{Q}_k, \hat{A})$—Error threshold function $F(\Psi, C)$—Error threshold value (E)

$\hat{\Omega}_k$—Iteration termination criteria, e.g., iteration count, $r^2$, standard error, etc.

Initial Computation, k=0

Initial Step 1: Using initial model coefficient estimates, $\hat{\beta}_{0\to 1}$, compute initial model predicted values by applying the model to the complete data set:

$$\hat{Q}_1=M(\hat{X}:\hat{\beta}_{0\to 1})$$

Initial step 2: Compute initial model performance results:

$$\hat{\Omega}_1=f(\hat{Q}_1,\hat{A},k=0,r^2,\text{standard error, etc.})$$

Initial Step 3: Compute model error threshold value(s):

$$E_1=F(\Psi(\hat{Q}_1,\hat{A}),C)$$

Initial Step 4: Filter the data records to remove outliers:

$$\hat{X}_1=\{\forall x\in\hat{X}|\Psi(\hat{Q}_1,\hat{A})<E_1\}$$

Iterative Computations, k>0

Iteration Step 1: Compute predicted values by applying the model to the accepted data set:

$$\hat{Q}_{k+1}=M(\hat{X}_k:\hat{\beta}_{k\to k+1})$$

Iteration Step 2: Compute model performance results:

$$\hat{\Omega}_{k+1}=f(\hat{Q}_{k+1},\hat{A},k,r^2,\text{standard error, etc.})$$

If termination criteria are achieved, stop, otherwise proceed to Step 3:

Iteration Step 3: Compute results for removed data, $\hat{X}_{Ck}=\{\forall x\in\hat{X}|x\notin\hat{X}_k\}$ using current model:

$$\hat{Q}_{Ck+1}=M(\hat{X}_{Ck}:\hat{\beta}_{k\to k+1})$$

Iteration Step 4: Compute model error threshold values:

$$E_{k+1}=F(\Psi(\hat{Q}_{k+1}+\hat{Q}_{Ck+1},\hat{A}),C)$$

Iteration Step 5: Filter the data records to remove outliers:

$$\hat{X}_{k+1}=\{\forall x\in\hat{X}|\Psi(\hat{Q}_{k+1}+\hat{Q}_{Ck+1},\hat{A})<E_{k+1}\}$$

Another mathematical description of one embodiment of Dynamic Outlier Bias Reduction is shown as follows:

Nomenclature $\hat{X}$—Set of all data records: $\hat{X}=\hat{X}_k+\hat{X}_{Ck}$, where:
- $\hat{X}_k$—Set of accepted data records for the $k^{th}$ iteration
- $\hat{X}_{Ck}$—Set of outlier (removed) data records for the $k^{th}$ iteration $\hat{Q}_k$—Set of computed model predicted values for $\hat{X}_k$ $\hat{X}_{Ck}$—Set of outlier model predicted values for $\hat{X}_{Ck}$ $\hat{A}$—Set of actual values (target values) on which the model is based $\hat{\beta}_{k\to k+1}$—Set of model coefficients at the $k+1^{st}$ iteration computed as a result of the model computations using $\hat{X}_k$ $M(\hat{X}_k:\hat{\beta}_{k\to k+1})$—Model computation producing $\hat{Q}_{k+1}$ from $\hat{X}_k$ storing model derived and user-supplied coefficients $\hat{\beta}_{k\to k+1}$ $C_{RE}$—User supplied relative error criterion (%)

$C_{AE}$—User supplied absolute error criterion (%)

$RE(\hat{Q}_k+\hat{Q}_{Ck}, \hat{A})$—Relative error values for all data records $AE(\hat{Q}_k+\hat{Q}_{Ck}, \hat{A})$—Absolute error values for all data records $P_{RE_k}$—Relative error threshold value for the $k^{th}$ iteration where $$P_{RE_k}=\text{Percentile}(RE(\hat{Q}_k+\hat{Q}_{Ck},\hat{A}),C_{RE})$$

$P_{AE_k}$—Absolute error threshold value for the $k^{th}$ iteration where $$P_{AE_k}=\text{Percentile}(AE(\hat{Q}_k+\hat{Q}_{Ck},\hat{A}),C_{AE})$$

$\hat{\Omega}_k$—Iteration termination criteria, e.g., iteration count, $r^2$, standard error, etc.

Initial Computation, k=0

Initial Step 1: Using initial model coefficient estimates, $\hat{\beta}_{0\to 1}$, compute initial model predicted value results by applying the model to the complete data set:

$$\hat{Q}_1=M(\hat{X}:\hat{\beta}_{0\to 1})$$

Initial Step 2: Compute initial model performance results:

$$\hat{\Omega}_1=f(\hat{Q}_1,\hat{A},k=0,r^2,\text{standard error,etc.})$$

Initial Step 3: Compute model error threshold values:

$$P_{RE_1}=\text{Percentile}(RE(\hat{Q}_1,\hat{A}),C_{RE})$$

$$P_{AE_1}=\text{Percentile}(AE(\hat{Q}_1,\hat{A}),C_{AE})$$

Initial Step 4: Filter the data records to remove outliers:

$$\hat{X}_1=\left\{\forall x\in\hat{X}\left|\begin{Bmatrix}RE(\hat{Q}_1,\hat{A})\\AE(\hat{Q}_1,\hat{A})\end{Bmatrix}<\begin{pmatrix}P_{RE}\\P_{AE}\end{pmatrix}_1\right.\right\}$$

Iterative Computations, k>0

Iteration Step 1: Compute model predicted values by applying the model to the outlier removed data set:

$$\hat{Q}_{k+1}=M(\hat{X}_k:\hat{\beta}_{k\to k+1})$$

Iteration Step 2: Compute model performance results:

$$\hat{\Omega}_{k+1}=f(\hat{Q}_{k+1},\hat{A},k,r^2,\text{standard error,etc.})$$

If termination criteria are achieved, stop, otherwise proceed to Step 3:

Iteration Step 3: Compute results for the removed data, $\hat{X}_{Ck}=\{\forall x\in\hat{X}|x\notin\hat{X}_k\}$ using current model:

$$\hat{Q}_{Ck+1}=M(\hat{X}_{Ck}:\hat{\beta}_{k\rightarrow k+1})$$

Iteration Step 4: Compute model error threshold values:

$$P_{RE_{k+1}}=\text{Percentile}(\text{RE}(\hat{Q}_{k+1}+\hat{Q}_{Ck+1},\hat{A}),C_{RE})$$

$$P_{AE_{k+1}}=\text{Percentile}(\text{AE}(\hat{Q}_{k+1}+\hat{Q}_{Ck+1},\hat{A}),C_{AE})$$

Iteration Step 5: Filter the data records to remove outliers:

$$\hat{X}_{k+1}=\left\{\forall\, x\in\hat{X}\left|\begin{Bmatrix}RE(\hat{Q}_{k+1}+\hat{Q}_{Ck+1},\hat{A})\\AE(\hat{Q}_{k+1}+\hat{Q}_{Ck+1},\hat{A})\end{Bmatrix}<\begin{pmatrix}P_{RE}\\P_{AE}\end{pmatrix}_{k+1}\right.\right\}$$

Increment k and proceed to Iteration Step 1.

After each iteration where new model coefficients are computed from the current censored dataset, the removed data from the previous iteration plus the current censored data are recombined. This combination encompasses all data values in the complete dataset. The current model coefficients are then applied to the complete dataset to compute a complete set of predicted values. The absolute and relative errors are computed for the complete set of predicted values and new bias criteria percentile threshold values are computed. A new censored dataset is created by removing all data values where the absolute or relative errors are greater than the threshold values and the nonlinear optimization model is then applied to the newly censored dataset computing new model coefficients. This process enables all data values to be reviewed every iteration for their possible inclusion in the model dataset. It is possible that some data values that were excluded in previous iterations will be included in subsequent iterations as the model coefficients converge on values that best fit the data.

In one embodiment, variations in GHG emissions can result in overestimation or underestimation of emission results leading to bias in model predicted values. These non-industrial influences, such as environmental conditions and errors in calculation procedures, can cause the results for a particular facility to be radically different from similar facilities, unless the bias in the model predicted values is removed. The bias in the model predicted values may also exist due to unique operating conditions.

The bias can be removed manually by simply removing a facility's data from the calculation if analysts are confident that a facility's calculations are in error or possess unique, extenuating characteristics. Yet, when measuring a facility performance from many different companies, regions, and countries, precise a priori knowledge of the data details is not realistic. Therefore any analyst-based data removal procedure has the potential for adding undocumented, non-data supported biases to the model results.

In one embodiment, Dynamic Outlier Bias Reduction is applied to a procedure that uses the data and a prescribed overall error criteria to determine statistical outliers that are removed from the model coefficient calculations. This is a data-driven process that identifies outliers using a data produced global error criteria using for example, the percentile function. The use of Dynamic Outlier Bias Reduction is not limited to the reduction of bias in model predicted values, and its use in this embodiment is illustrative and exemplary only. Dynamic Outlier Bias Reduction may also be used, for example, to remove outliers from any statistical data set, including use in calculation of, but not limited to, arithmetic averages, linear regressions, and trend lines. The outlier facilities are still ranked from the calculation results, but the outliers are not used in the filtered data set applied to compute model coefficients or statistical results.

A standard procedure, commonly used to remove outliers, is to compute the standard deviation (σ) of the data set and simply define all data outside a 2σ interval of the mean, for example, as outliers. This procedure has statistical assumptions that, in general, cannot be tested in practice. The Dynamic Outlier Bias Reduction method description applied in an embodiment of this invention, is outlined in FIG. 1, uses both a relative error and absolute error. For example: for a facility, 'm':

$$\text{Relative Error}_m((\text{Predicted Value}_m-\text{Actual Value}_m)/\text{Actual Value}_m)^2 \quad (1)$$

$$\text{Absolute Error}_m(\text{Predicted Value}_m-\text{Actual Value}_m)^2 \quad (2)$$

$$\text{Absolut Error}_k=(\text{Model Results}_k-\text{Actual Emissions}_k)^2$$

In Step 110, the analyst specifies the error threshold criteria that will define outliers to be removed from the calculations. For example using the percentile operation as the error function, a percentile value of 80 percent for relative and absolute errors could be set. This means that data values less than the 80th percentile value for a relative error and less than the 80th percentile value for absolute error calculation will be included and the remaining values are removed or considered as outliers. In this example, for a data value to avoid being removed, the data value must be less than both the relative and absolute error 80th percentile values. However, the percentile thresholds for relative and absolute error may be varied independently, and, in another embodiment, only one of the percentile thresholds may be used.

In Step 120, the model standard error and coefficient of determination ($r^2$) percent change criteria are specified. While the values of these statistics will vary from model to model, the percent change in the preceding iteration procedure can be preset, for example, at 5 percent. These values can be used to terminate the iteration procedure. Another termination criteria could be the simple iteration count.

In Step 130, the optimization calculation is performed, which produces the model coefficients and predicted values for each facility.

In Step 140, the relative and absolute errors for all facilities are computed using Eqns. (1) and (2).

In Step 150, the error function with the threshold criteria specified in Step 110 is applied to the data computed in Step 140 to determine outlier threshold values.

In Step 160, the data is filtered to include only facilities where the relative error, absolute error, or both errors, depending on the chosen configuration, are less than the error threshold values computed in Step 150.

In Step 170, the optimization calculation is performed using only the outlier removed data set.

In Step 180, the percent change of the standard error and $r^2$ are compared with the criteria specified in Step 120. If the percent change is greater than the criteria, the process is repeated by returning to Step 140. Otherwise, the iteration procedure is terminated in step 190 and the resultant model computed from this Dynamic Outlier Bias Reduction criteria procedure is completed. The model results are applied to all facilities regardless of their current iterative past removed or admitted data status.

In another embodiment, the process begins with the selection of certain iterative parameters, specifically:

(1) an absolute error and relative error percentile value wherein one, the other or both may be used in the iterative process, (2) a coefficient of determination (also known as $r^2$) improvement value, and (3) a standard error improvement value.

The process begins with an original data set, a set of actual data, and either at least one coefficient or a factor used to calculate predicted values based on the original data set. A coefficient or set of coefficients will be applied to the original data set to create a set of predicted values. The set of coefficients may include, but is not limited to, scalars, exponents, parameters, and periodic functions. The set of predicted data is then compared to the set of actual data. A standard error and a coefficient of determination are calculated based on the differences between the predicted and actual data. The absolute and relative error associated with each one of the data points is used to remove data outliers based on the user-selected absolute and relative error percentile values. Ranking the data is not necessary, as all data falling outside the range associated with the percentile values for absolute and/or relative error are removed from the original data set. The use of absolute and relative errors to filter data is illustrative and for exemplary purposes only, as the method may be performed with only absolute or relative error or with another function.

The data associated with the absolute and relative error within a user-selected percentile range is the outlier removed data set, and each iteration of the process will have its own filtered data set. This first outlier removed data set is used to determine predicted values that will be compared with actual values. At least one coefficient is determined by optimizing the errors, and then the coefficient is used to generate predicted values based on the first outlier removed data set. The outlier bias reduced coefficients serve as the mechanism by which knowledge is passed from one iteration to the next.

After the first outlier removed data set is created, the standard error and coefficient of determination are calculated and compared with the standard error and coefficient of determination of the original data set. If the difference in standard error and the difference in coefficient of determination are both below their respective improvement values, then the process stops. However, if at least one of the improvement criteria is not met, then the process continues with another iteration. The use of standard error and coefficient of determination as checks for the iterative process is illustrative and exemplary only, as the check can be performed using only the standard error or only the coefficient of determination, a different statistical check, or some other performance termination criteria (such as number of iterations).

Assuming that the first iteration fails to meet the improvement criteria, the second iteration begins by applying the first outlier bias reduced data coefficients to the original data to determine a new set of predicted values. The original data is then processed again, establishing absolute and relative error for the data points as well as the standard error and coefficient of determination values for the original data set while using the first outlier removed data set coefficients. The data is then filtered to form a second outlier removed data set and to determine coefficients based on the second outlier removed data set.

The second outlier removed data set, however, is not necessarily a subset of the first outlier removed data set and it is associated with second set of outlier bias reduced model coefficients, a second standard error, and a second coefficient of determination. Once those values are determined, the second standard error will be compared with the first standard error and the second coefficient of determination will be compared against the first coefficient of determination.

If the improvement value (for standard error and coefficient of determination) exceeds the difference in these parameters, then the process will end. If not, then another iteration will begin by processing the original data yet again; this time using the second outlier bias reduced coefficients to process the original data set and generate a new set of predicted values. Filtering based on the user-selected percentile value for absolute and relative error will create a third outlier removed data set that will be optimized to determine a set of third outlier bias reduced coefficients. The process will continue until the error improvement or other termination criteria are met (such as a convergence criteria or a specified number of iterations).

The output of this process will be a set of coefficients or model parameters, wherein a coefficient or model parameter is a mathematical value (or set of values), such as, but not limited to, a model predicted value for comparing data, slope and intercept values of a linear equation, exponents, or the coefficients of a polynomial. The output of Dynamic Outlier Bias Reduction will not be an output value of its own right, but rather the coefficients that will modify data to determine an output value.

In another embodiment, illustrated in FIG. 2, Dynamic Outlier Bias Reduction is applied as a data quality technique to evaluate the consistency and accuracy of data to verify that the data is appropriate for a specific use. For data quality operations, the method may not involve an iterative procedure. Other data quality techniques may be used alongside Dynamic Outlier Bias Reduction during this process. The method is applied to the arithmetic average calculation of a given data set. The data quality criteria, for this example is that the successive data values are contained within some range. Thus, any values that are spaced too far apart in value would constitute poor quality data. Error terms are then constructed of successive values of a function and Dynamic Outlier Bias Reduction is applied to these error values.

In Step 210 the initial data is listed in any order.

Step 220 constitutes the function or operation that is performed on the dataset. In this embodiment example, the function and operation is the ascending ranking of the data followed by successive arithmetic average calculations where each line corresponds to the average of all data at and above the line.

Step 230 computes the relative and absolute errors from the data using successive values from the results of Step 220.

Step 240 allows the analyst to enter the desired outlier removal error criteria (%). The Quality Criteria Value is the resultant value from the error calculations in Step 230 based on the data in Step 220.

Step 250 shows the data quality outlier filtered dataset. Specific values are removed if the relative and absolute errors exceed the specified error criteria given in Step 240.

Step 260 shows the arithmetic average calculation comparison between the complete and outlier removed datasets. The analyst is the final step as in all applied mathematical or statistical calculations judging if the identified outlier removed data elements are actually poor quality or not. The Dynamic Outlier Bias Reduction system and method eliminates the analyst from directly removing data but best practice guidelines suggest the analyst review and check the results for practical relevance.

In another embodiment illustrated in FIG. 3, Dynamic Outlier Bias Reduction is applied as a data validation technique that tests the reasonable accuracy of a data set to determine if the data are appropriate for a specific use. For data validation operations, the method may not involve an iterative procedure. In this example, Dynamic Outlier Bias Reduction is applied to the calculation of the Pearson Correlation Coefficient between two data sets. The Pearson Correlation Coefficient can be sensitive to values in the data set that are relatively different than the other data points. Validating the data set with respect to this statistic is important to ensure that the result represents what the majority of data suggests rather than influence of extreme values. The data validation process for this example is that successive data values are contained within a specified range. Thus, any values that are spaced too far apart in value (e.g. outside the specified range) would signify poor quality data. This is accomplished by constructing the error terms of successive values of the function. Dynamic Outlier Bias Reduction is applied to these error values, and the outlier removed data set is validated data.

In Step 310, the paired data is listed in any order.

Step 320 computes the relative and absolute errors for each ordered pair in the dataset.

Step 330 allows the analyst to enter the desired data validation criteria. In the example, both 90% relative and absolute error thresholds are selected. The Quality Criteria Value entries in Step 330 are the resultant absolute and relative error percentile values for the data shown in Step 320.

Step 340 shows the outlier removal process where data that may be invalid is removed from the dataset using the criteria that the relative and absolute error values both exceed the values corresponding to the user selected percentile values entered in Step 330. In practice other error criteria may be used and when multiple criteria are applied as shown in this example, any combination of error values may be applied to determine the outlier removal rules.

Step 350 computes the data validated and original data values statistical results. In this case, the Pearson Correlation Coefficient. These results are then reviewed for practical relevance by the analyst.

In another embodiment, Dynamic Outlier Bias Reduction is used to perform a validation of an entire data set. Standard error improvement value, coefficient of determination improvement value, and absolute and relative error thresholds are selected, and then the data set is filtered according to the error criteria. Even if the original data set is of high quality, there will still be some data that will have error values that fall outside the absolute and relative error thresholds. Therefore, it is important to determine if any removal of data is necessary. If the outlier removed data set passes the standard error improvement and coefficient of determination improvement criteria after the first iteration, then the original data set has been validated, since the filtered data set produced a standard error and coefficient of determination that too small to be considered significant (e.g. below the selected improvement values).

In another embodiment, Dynamic Outlier Bias Reduction is used to provide insight into how the iterations of data outlier removal are influencing the calculation. Graphs or data tables are provided to allow the user to observe the progression in the data outlier removal calculations as each iteration is performed. This stepwise approach enables analysts to observe unique properties of the calculation that can add value and knowledge to the result. For example, the speed and nature of convergence can indicate the influence of Dynamic Outlier Bias Reduction on computing representative factors for a multi-dimensional data set.

As an illustration, consider a linear regression calculation over a poor quality data set of 87 records. The form of the equation being regressed is y=mx+b. Table 1 shows the results of the iterative process for 5 iterations. Notice that using relative and absolute error criteria of 95%, convergence is achieved in 3 iterations. Changes in the regression coefficients can be observed and the Dynamic Outlier Bias Reduction method reduced the calculation data set based on 79 records. The relatively low coefficient of determination ($r^2$=39%) suggests that a lower (<95%) criteria should be tested to study the additional outlier removal effects on the $r^2$ statistic and on the computed regression coefficients.

TABLE 1

Dynamic Outlier Bias Reduction Example: Linear Regression at 95%

| Iteration | N | Error | $r^2$ | m | b |
|---|---|---|---|---|---|
| 0 | 87 | 3.903 | 25% | −0.428 | 41.743 |
| 1 | 78 | 3.048 | 38% | −0.452 | 43.386 |
| 2 | 83 | 3.040 | 39% | −0.463 | 44.181 |
| 3 | 79 | 3.030 | 39% | −0.455 | 43.630 |
| 4 | 83 | 3.040 | 39% | −0.463 | 44.181 |
| 5 | 79 | 3.030 | 39% | −0.455 | 43.630 |

In Table 2 the results of applying Dynamic Outlier Bias Reduction are shown using the relative and absolute error criteria of 80%. Notice that a 15 percentage point (95% to 80%) change in outlier error criteria produced 35 percentage point (39% to 74%) increase in $r^2$ with a 35% additional decrease in admitted data (79 to 51 records included). The analyst can use a graphical view of the changes in the regression lines with the outlier removed data and the numerical results of Tables 1 and 2 in the analysis process to communicate the outlier removed results to a wider audience and to provide more insights regarding the effects of data variability on the analysis results.

TABLE 2

Dynamic Outlier Bias Reduction Example: Linear Regression at 80%

| Iteration | N | Error | $r^2$ | m | b |
|---|---|---|---|---|---|
| 0 | 87 | 3.903 | 25% | −0.428 | 41.743 |
| 1 | 49 | 1.607 | 73% | −0.540 | 51.081 |
| 2 | 64 | 1.776 | 68% | −0.561 | 52.361 |
| 3 | 51 | 1.588 | 74% | −0.558 | 52.514 |
| 4 | 63 | 1.789 | 68% | −0.559 | 52.208 |
| 5 | 51 | 1.588 | 74% | −0.558 | 52.514 |

Figure 4:
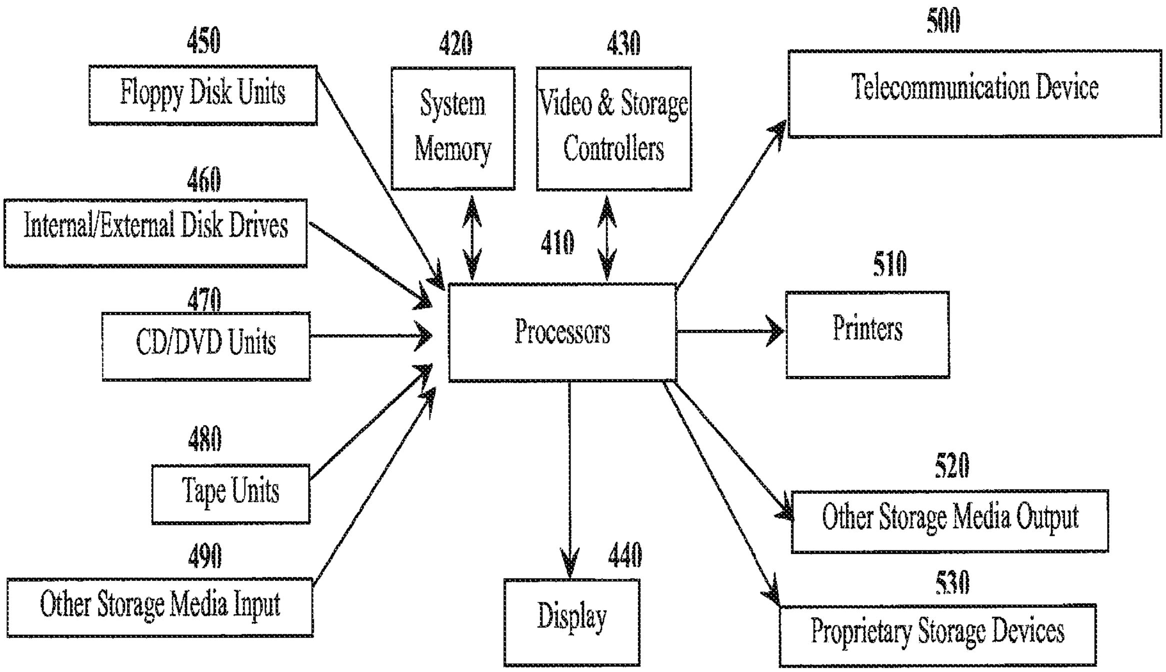
FIG. 4 is an illustrative node for implementing a method of the invention.

As illustrated in FIG. 4, one embodiment of system used to perform the method includes a computing system. The hardware consists of a processor 410 that contains adequate system memory 420 to perform the required numerical computations. The processor 410 executes a computer program residing in system memory 420 to perform the method. Video and storage controllers 430 may be used to enable the operation of display 440. The system includes various data storage devices for data input such as floppy disk units 450, internal/external disk drives 460, internal CD/DVDs 470, tape units 480, and other types of electronic storage media 490. The aforementioned data storage devices are illustrative and exemplary only. These storage media are used to enter data set and outlier removal criteria into to the system, store the outlier removed data set, store calculated factors, and store the system-produced trend lines and trend line iteration graphs. The calculations can apply statistical software packages or can be performed from the data entered in spreadsheet formats using Microsoft Excel, for example. The calculations are performed using either customized software programs designed for company-specific system implementations or by using commercially available software that is compatible with Excel or other database and spreadsheet programs. The system can also interface with proprietary or public external storage media 300 to link with other databases to provide data to be used with the Dynamic Outlier Bias Reduction system and method calculations. The output devices can be a telecommunication device 510 to transmit the calculation worksheets and other system produced graphs and reports via an intranet or the Internet to management or other personnel, printers 520, electronic storage media similar to those mentioned as input devices 450, 460, 470, 480, 490 and proprietary storage databases 530. These output devices used herein are illustrative and exemplary only.

As illustrated in FIGS. 5, 6A, 6B, 7A, 7B, 8A, and 8B, in one embodiment, Dynamic Outlier Bias Reduction can be used to quantitatively and qualitatively assess the quality of the data set based on the error and correlation of the data set's data values, as compared to the error and correlation of a benchmark dataset comprised of random data values developed from within an appropriate range. In one embodiment, the error can be designated to be the data set's standard error, and the correlation can be designated to be the data set's coefficient of determination ($r^2$). In another embodiment, correlation can be designated to be the Kendall rank correlation coefficient, commonly referred to as Kendall's tau (T) coefficient. In yet another embodiment, correlation can be designated to be the Spearman's rank correlation coefficient, or Spearman's p (rho) coefficient. As explained above, Dynamic Outlier Bias Reduction is used to systematically remove data values that are identified as outliers, not representative of the underlying model or process being described. Normally, outliers are associated with a relatively small number of data values. In practice, however, a dataset could be unknowingly contaminated with spurious values or random noise. The graphical illustration of FIGS. 5, 6A, 6B, 7A, 7B, 8A, and 8B illustrate how the Dynamic Outlier Bias Reduction system and method can be applied to identify situations where the underlying model is not supported by the data. The outlier reduction is performed by removing data values for which the relative and/or absolute errors, computed between the model predicted and actual data values, are greater than a percentile-based bias criteria, e.g. 80%. This means that the data values are removed if either the relative or absolute error percentile values are greater than the percentile threshold values associated with the 80th percentile (80% of the data values have an error less than this value.)

Figure 5:
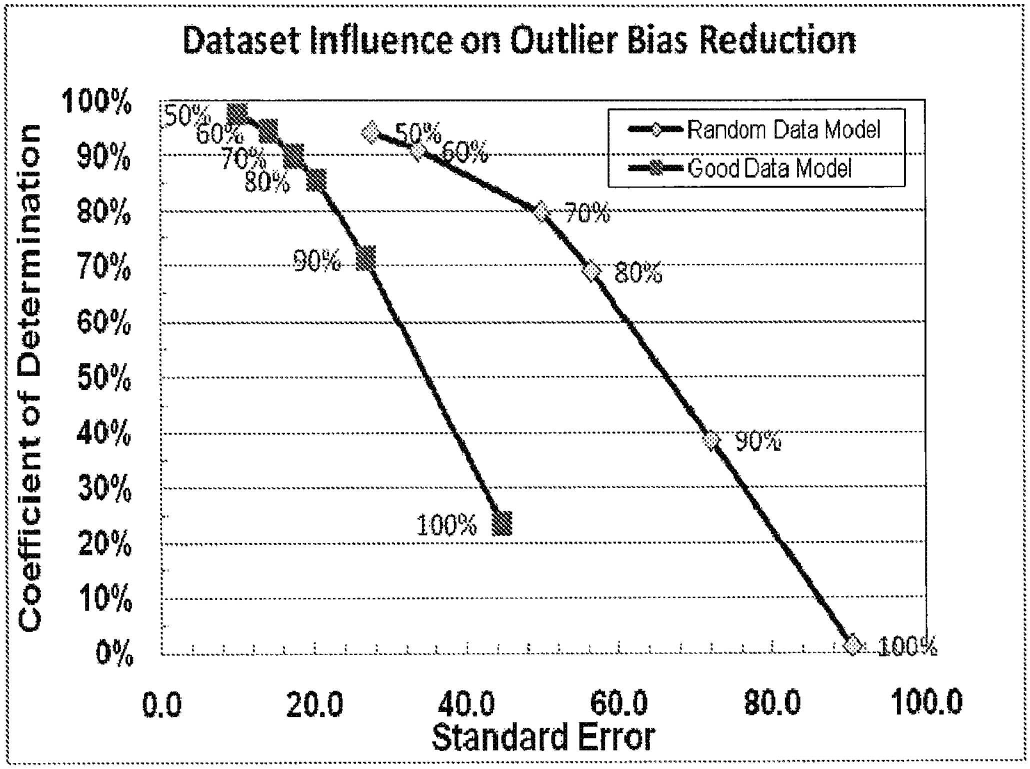
FIG. 5 is an illustrative graph for quantitative assessment of a data set.

As illustrated in FIG. 5, both a realistic model development dataset and a dataset of random values developed within the range of the actual dataset are compared. Because in practice the analysts typically do not have prior knowledge of any dataset contamination, such realization must come from observing the iterative results from several model calculations using the dynamic outlier bias reduction system and method. FIG. 5 illustrates an exemplary model development calculation results for both datasets. The standard error, a measure of the amount of model unexplained error, is plotted versus the coefficient of determination (%) or $r^2$, representing how much data variation is explained by the model. The percentile values next to each point represent the bias criteria. For example, 90% signifies that data values for relative or absolute error values greater than the 90th percentile are removed from the model as outliers. This corresponds to removing 10% of the data values with the highest errors each iteration.

As FIG. 5 illustrates, for both the random and realistic dataset models, error is reduced by increasing the bias criteria, i.e., the standard error and the coefficient of determination are improved for both datasets. However, the standard error for the random dataset is two to three times larger than the realistic model dataset. The analyst may use a coefficient of determination requirement of 80%, for example, as an acceptable level of precision for determining model parameters. In FIG. 5, an $r^2$ of 80% is achieved at a 70% bias criteria for the random dataset, and at an approximately 85% bias criteria for the realistic data. However, the corresponding standard error for the random dataset is over twice as large as the realistic dataset. Thus, by systematically running the model dataset analysis with different bias criteria and repeating the calculations with a representative spurious dataset and plotting the result as shown in FIG. 5, analysts can assess acceptable bias criteria (i.e., the acceptable percentage of data values removed) for a data set, and accordingly, the overall dataset quality. Moreover, such systematic model dataset analysis may be used to automatically render advice regarding the viability of a data set as used in developing a model based on a configurable set of parameters. For example, in one embodiment wherein a model is developed using Dynamic Outlier Bias Removal for a dataset, the error and correlation coefficient values for the model dataset and for a representative spurious dataset, calculated under different bias criteria, may be used to automatically render advice regarding the viability of the data set in supporting the developed model, and inherently, the viability of the developed model in supporting the dataset.

As illustrated in FIG. 5, observing the behavior of these model performance values for several cases provides a quantitative foundation for determining whether the data values are representative of the processes being modeled. For example, referring to FIG. 5, the standard error for the realistic data set at a 100% bias criteria (i.e., no bias reduction), corresponds to the standard error for the random data set at approximately 65% bias criteria (i.e., 35% of the data values with the highest errors removed). Such a finding supports the conclusion that data is not contaminated.

In addition to the above-described quantitative analysis facilitated by the illustrative graph of FIG. 5, Dynamic Outlier Bias Reduction can be utilized in an equally, if not more powerful, subjective procedure to help assess a dataset's quality. This is done by plotting the model predicted values against the data given actual target values for both the outlier and included results.

Figure 6A:
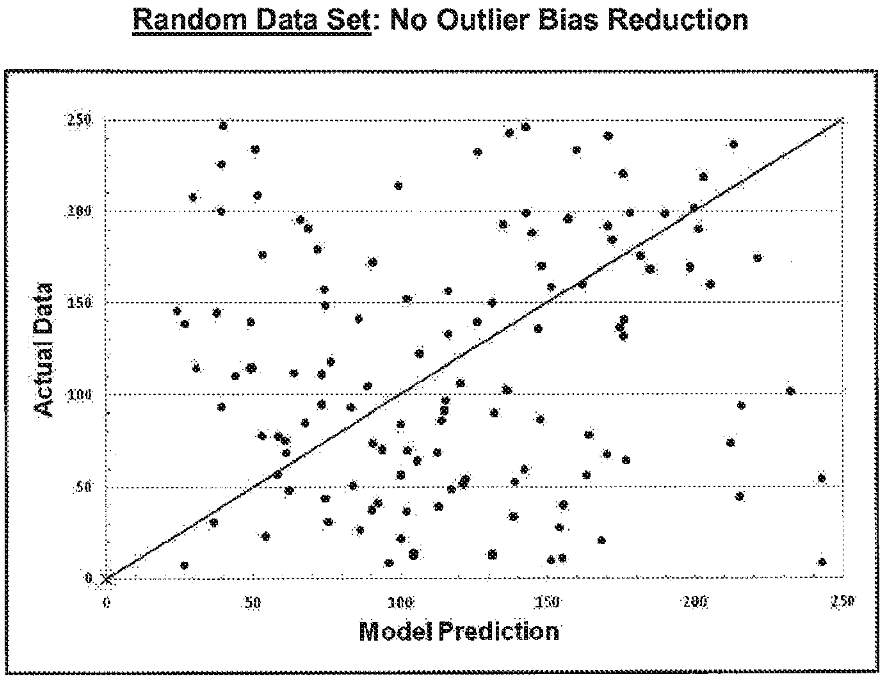
FIGS. 6A and 6B are illustrative graphs for qualitative assessment of the data set of FIG. 5, illustrating the randomized and realistic data set, respectively, for the entire data set.
Figure 6B:
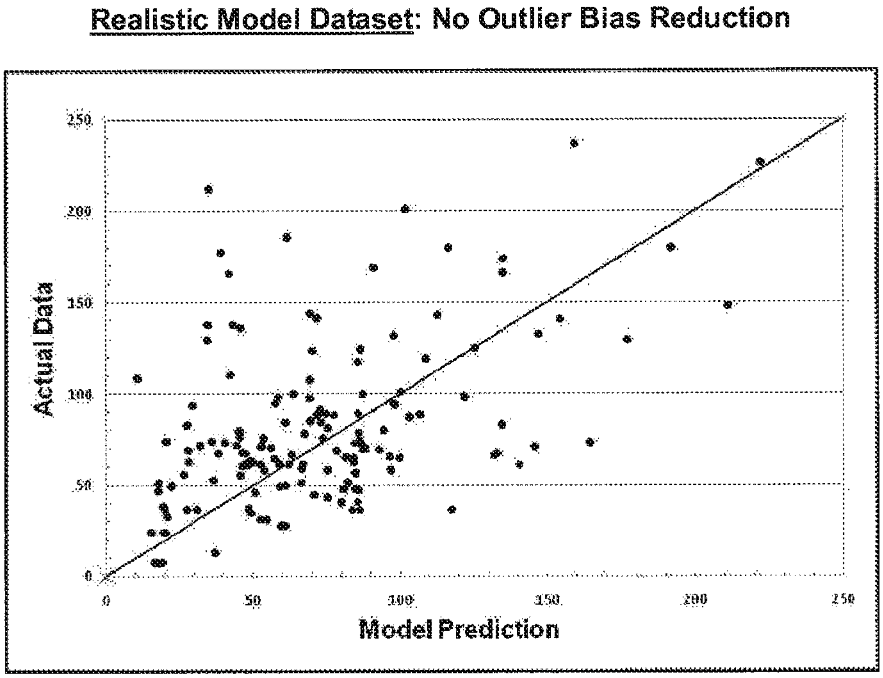

FIGS. 6A and 6B illustrate these plots for the 100% points of both the realistic and random curves in FIG. 5. The large scatter in FIG. 6A is consistent with the arbitrary target values and the resultant inability of the model to fit this intentional randomness. FIG. 6B is consistent and common with the practical data collection in that the model prediction and actual values are more grouped around the line whereon model predicted values equal actual target values (hereinafter Actual=Predicted line).

Figure 7A:
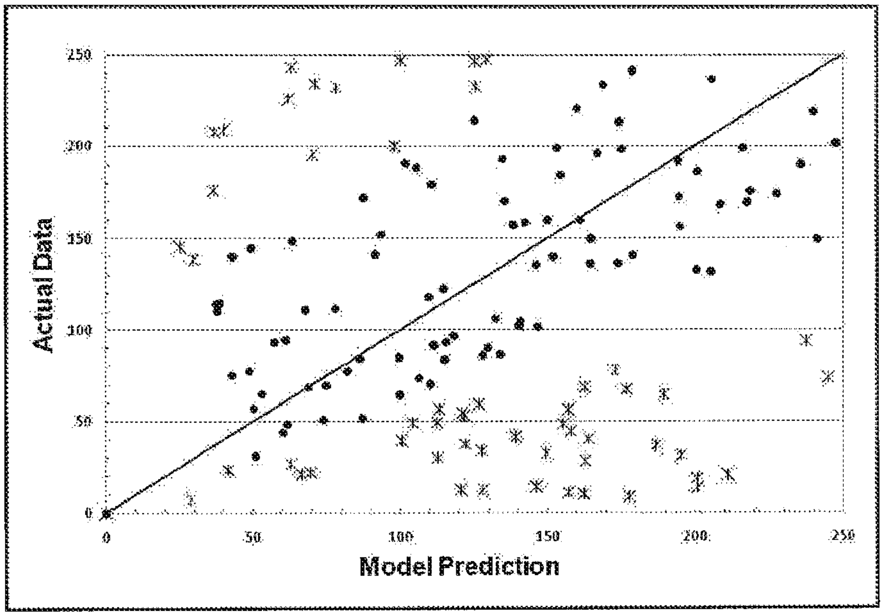
FIGS. 7A and 7B are illustrative graphs for qualitative assessment of the data set of FIG. 5, illustrating the randomized and realistic data set, respectively, after removal of 30% of the data as outliers.
Figure 7B:
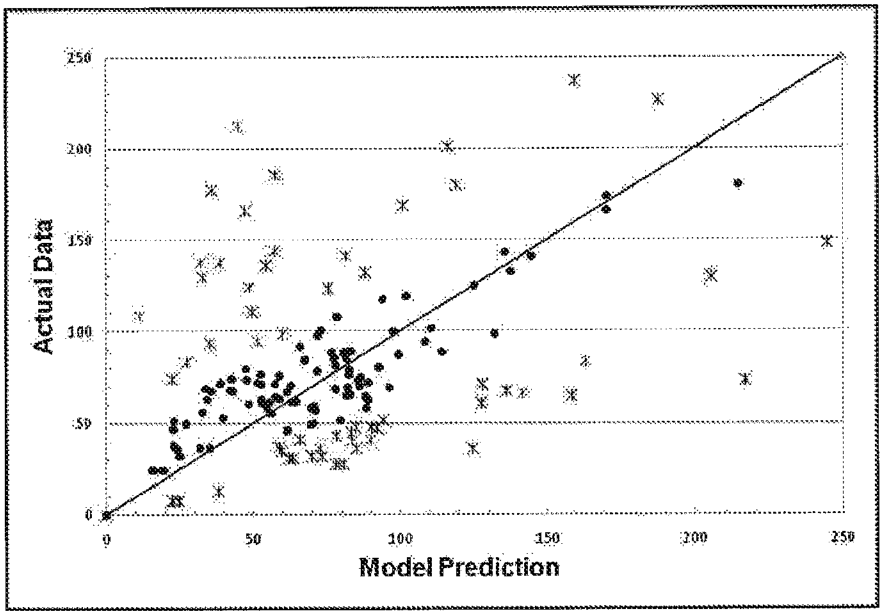

FIGS. 7A and 7B illustrate the results from the 70% points in FIG. 5 (i.e., 30% of data removed as outliers). In FIGS. 7A and 7B the outlier bias reduction is shown to remove the points most distant from the Actual=Predicted line, but the large variation in model accuracy between FIGS. 7A and 7B suggests that this dataset is representative of the processes being modeled.

Figure 8A:
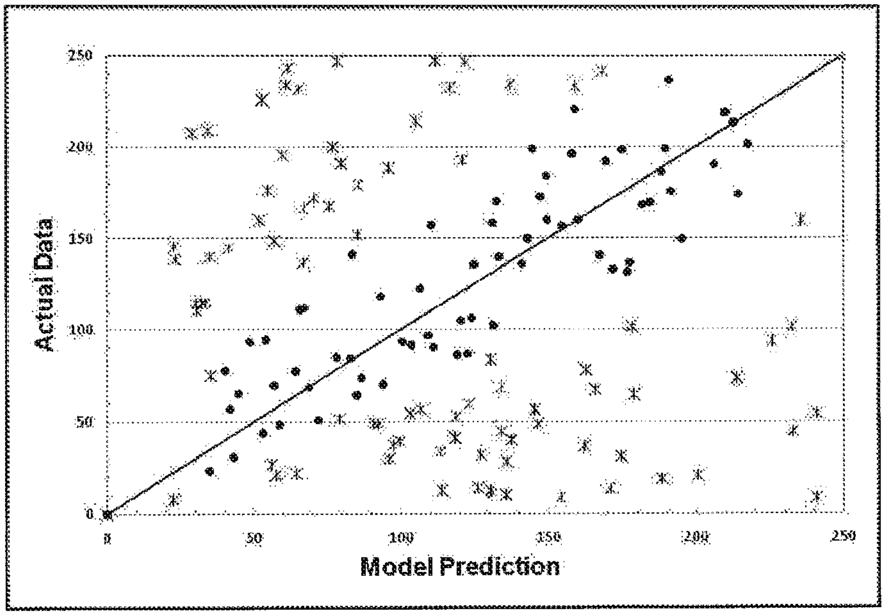
FIGS. 8A and 8B are illustrative graphs for qualitative assessment of the data set of FIG. 5, illustrating the randomized and realistic data set, respectively, after removal of 50% of the data as outliers.
Figure 8B:
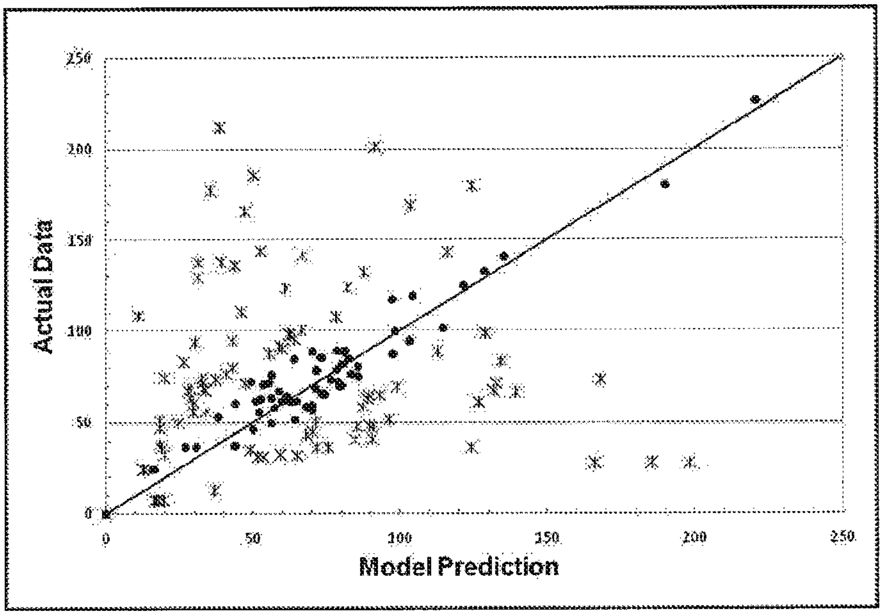

FIGS. 8A and 8B show the results from the 50% points in FIG. 5 (i.e., 50% of data removed as outliers). In this case about half of the data is identified as outliers and even with this much variation removed from the dataset, the model, in FIG. 8A, still does not closely describe the random dataset. The general variation around the Actual=Predicted line is about the same as in the FIGS. 6A and 7A taking into account the removed data in each case. FIG. 8B shows that with 50% of the variability removed, the model was able to produce predicted results that closely match the actual data. Analyzing these types of visual plots in addition to the analysis of performance criteria shown in FIG. 5 can be used by analysts to assess the quality of actual datasets in practice for model development. While FIGS. 5, 6A, 6B, 7A, 7B, 8A, and 8B illustrate visual plots wherein the analysis is based on performance criteria trends corresponding to various bias criteria values, in other embodiments, the analysis can be based on other variables that correspond to bias criteria values, such as model coefficient trends corresponding to various bias criteria selected by the analyst.

The foregoing disclosure and description of the preferred embodiments of the invention are illustrative and explanatory thereof and it will be understood by those skilled in the art that various changes in the details of the illustrated system and method may be made without departing from the scope of the invention.

What is claimed is:

1. A computer implemented method comprising:

generating an operation-related random data set based on a current operation-related actual data set;

iteratively refining, by at least one processor, a set of model parameters of at least one machine learning model until a termination criterion is met, wherein the iteratively refining comprises iteratively repeating steps comprising:

determining a plurality of model predicted values using the set of model parameters of the at least one machine learning model based on the current operation-related actual data set, determining an outlier data set and a non-outlier data set associated with the current operation-related actual data set based at least in part on:

an error of each model predicted value relative to each actual value of a training data set, and at least one bias criteria;

training the at least one machine learning model using the non-outlier data set to update the set of model parameters;

utilizing the model to generate at least one outlier bias reduced, operation-related data set for at least one operational variable based on the current operation-related actual data set and the operation-related random data set;

determining a correlation between the at least one outlier bias reduced, operation-related actual data set and the at least one outlier bias reduced, operation-related random data set based at least in part on a correlation measure;

determining, based on the correlation being less than a predetermined threshold, at least one operational standard for at least one operational process based on the at least one outlier bias reduced, operation-related actual data set for each operational variable; and causing the at least one operation standard to be utilized in monitoring a performance consistency of the at least one operational process across a plurality of operations.

2. The method of claim 1, wherein iteratively reining refining the set of model parameters further comprises:

iteratively performing one or more iterations of outlier bias reduction in the facility operating data of the plurality of facilities based at least in part on the model;

wherein the iteratively performing the one or more iterations of outlier bias reduction comprises steps of:

(i) determining a set of model-predicted values;

(ii) comparing the set of model-predicted values to the facility operating data to produce a set of error values;

(iii) removing bias facility operating data of one or more performance outlier facilities from the facility operating data of the plurality of facilities to form a non-biased facility operating data of one or more performance non-biased facilities that are selected from the plurality of facilities, wherein the one or more performance outlier facilities are determined based at least in part on the set of error values and the one or more acceptable bias criteria;

(iv) constructing, based at least in part on the non-biased facility operating a data, an updated model for the one or more operating conditions, wherein the updated model comprises one or more updated coefficients;

(v) repeating steps (i) through (iv) when one or more termination criteria are not satisfied;

determining, by the processor, based at least in part on the non-biased facility operating data for the one or more operating conditions of the one or more performance non-biased facilities, one or more non-biased performance standards for the one or more operating conditions; and tracking, by processor, based at least in part on the one or more non-biased performance standards and the facility operating data, operating performance of each respective facility of the plurality of facilities so that operating performance comports with the one or more non-biased performance standards.

3. The method of claim 2, wherein the iteratively performing the one or more iterations of the outlier bias reduction further comprises the steps of:

determining at least one set of first improvement error values for the facility operating data;

determining a set of second improvement error values for the non-biased facility operating data; and comparing the at least one set of first improvement error values with the at least one set of second improvement error values.

4. The method of claim 3, wherein the determination that the one or more termination criteria are not satisfied is based on a comparison of the at least one set of first improvement error values with the at least one set of second improvement error values.

5. The method of claim 4, wherein the determination that the one or more termination criteria are not satisfied is based on determining that the one or more termination criteria have at least one improvement value that does not exceed a difference of the at least one set of first improvement error values and the at least one set of second improvement error values.

6. The method of claim 3, wherein the first improvement error values are standard error values.

7. The method of claim 3, wherein the first improvement error values are coefficient of determination values.

8. The method of claim 2, wherein a particular criterium is a specified number of iterations.

9. The method of claim 2, wherein a particular criterium is a convergence criterium.

10. The method of claim 2, wherein the set of error values comprises a set of relative error values and a set of absolute error values.

11. The method of claim 10, wherein the one or more performance outlier facilities are determined as one or more facilities that have the relative error values and the absolute error values for respective facility operating data exceed one or more error threshold criteria associated with the one or more acceptable bias criteria.

12. The method of claim 2, wherein the repeating steps i) through (iv) further comprises:

recombining the non-biased facility operating data of one or more performance non-biased facilities with the bias facility operating data of the one or more performance outlier facilities to produce the facility operating data.

* * * * *